United States Patent
Khosravi et al.

(10) Patent No.: US 8,044,137 B2
(45) Date of Patent: Oct. 25, 2011

(54) MATERIALS FORMABLE IN SITU WITHIN A MEDICAL DEVICE

(75) Inventors: Farhad Khosravi, Los Altos Hills, CA (US); James Dreher, Santa Monica, CA (US)

(73) Assignee: Incept LLC, Lexington, MA (US)

( * ) Notice: Subject to any disclaimer, the term of this patent is extended or adjusted under 35 U.S.C. 154(b) by 0 days.

(21) Appl. No.: 12/970,515

(22) Filed: Dec. 16, 2010

(65) Prior Publication Data

US 2011/0092613 A1 Apr. 21, 2011

Related U.S. Application Data

(63) Continuation of application No. 11/443,504, filed on May 30, 2006, now Pat. No. 7,872,068.

(51) Int. Cl.
- *C08L 33/06* (2006.01)
- *A61M 29/04* (2006.01)
- *A61F 2/02* (2006.01)
- *A61F 2/94* (2006.01)

(52) U.S. Cl. ........ 524/560; 606/192; 623/1.21; 623/926

(58) Field of Classification Search .................. 524/560; 606/192; 623/1.21, 926

See application file for complete search history.

(56) References Cited

U.S. PATENT DOCUMENTS

| | | |
|---|---|---|
| 3,833,003 A | 9/1974 | Taricco |
| 4,311,146 A | 1/1982 | Wonder |
| 4,341,218 A | 7/1982 | Ü |
| 4,351,922 A | 9/1982 | Yoshida et al. |
| 4,490,497 A | 12/1984 | Evrard et al. |
| 4,641,653 A | 2/1987 | Rockey |
| 4,703,108 A | 10/1987 | Silver |
| 4,728,328 A | 3/1988 | Hughes et al. |
| 4,826,945 A | 5/1989 | Cohn et al. |
| 4,938,763 A | 7/1990 | Dunn et al. |
| 5,100,992 A | 3/1992 | Cohn et al. |
| 5,258,042 A | 11/1993 | Mehta |
| 5,266,325 A | 11/1993 | Kuzma et al. |
| 5,272,012 A | 12/1993 | Opolski |
| 5,376,375 A | 12/1994 | Rhee et al. |
| 5,410,016 A | 4/1995 | Hubbell et al. |
| 5,456,693 A | 10/1995 | Conston et al. |
| 5,462,990 A | 10/1995 | Hubbell et al. |
| 5,464,396 A | 11/1995 | Barta et al. |
| 5,510,418 A | 4/1996 | Rhee et al. |
| 5,514,379 A | 5/1996 | Weissleder et al. |
| 5,530,528 A | 6/1996 | Houki et al. |
| 5,534,024 A | 7/1996 | Rogers et al. |
| 5,583,114 A | 12/1996 | Barrows et al. |
| 5,587,175 A | 12/1996 | Viegas et al. |
| 5,603,991 A | 2/1997 | Kupiecki et al. |
| 5,624,685 A | 4/1997 | Takahashi et al. |
| 5,627,233 A | 5/1997 | Hubbell et al. |
| 5,629,008 A | 5/1997 | Lee |
| 5,660,849 A | 8/1997 | Polson et al. |
| 5,665,117 A | 9/1997 | Rhodes |
| 5,665,840 A | 9/1997 | Pohlmann et al. |
| 5,668,236 A | 9/1997 | Engelhardt et al. |
| 5,672,662 A | 9/1997 | Harris et al. |
| 5,690,671 A | 11/1997 | McGurk et al. |
| 5,693,088 A | 12/1997 | Lazarus |
| 5,714,159 A | 2/1998 | Shalaby |
| 5,752,974 A | 5/1998 | Rhee et al. |
| 5,769,882 A | 6/1998 | Fogarty et al. |
| 5,823,198 A | 10/1998 | Jones et al. |
| 5,824,037 A | 10/1998 | Fogarty et al. |
| 5,843,160 A | 12/1998 | Rhodes et al. |
| 5,851,508 A | 12/1998 | Greff et al. |
| 5,874,500 A | 2/1999 | Rhee et al. |
| 5,876,448 A | 3/1999 | Thompson et al. |
| 5,932,462 A | 8/1999 | Harris et al. |
| 5,962,023 A | 10/1999 | Jamiolkowski et al. |
| 5,994,750 A | 11/1999 | Yagi |
| 6,031,148 A | 2/2000 | Hayes et al. |
| 6,063,061 A | 5/2000 | Wallace et al. |
| 6,110,198 A | 8/2000 | Fogarty et al. |
| 6,129,761 A | 10/2000 | Hubbell |
| 6,152,943 A | 11/2000 | Sawhney |
| 6,168,592 B1 | 1/2001 | Kupiecki et al. |
| 6,190,402 B1 | 2/2001 | Horton et al. |
| 6,193,745 B1 | 2/2001 | Fogarety et al. |
| 6,196,230 B1 | 3/2001 | Hall et al. |
| 6,201,065 B1 | 3/2001 | Pathak et al. |
| 6,206,930 B1 | 3/2001 | Burg et al. |
| 6,251,382 B1 | 6/2001 | Greenwald et al. |
| 6,258,870 B1 | 7/2001 | Hubbell et al. |
| 6,261,305 B1 | 7/2001 | Marotta et al. |
| 6,261,544 B1 | 7/2001 | Coury et al. |
| 6,268,405 B1 | 7/2001 | Yao et al. |
| 6,271,278 B1 | 8/2001 | Park et al. |
| 6,283,991 B1 | 9/2001 | Cox et al. |
| 6,296,603 B1 | 10/2001 | Turnlund et al. |

(Continued)

FOREIGN PATENT DOCUMENTS

EP 0 732 109 A1 9/1996

(Continued)

OTHER PUBLICATIONS

Gander et al., Crosslinked Poly(Alkylene Oxides) for the Preparation of Controlled Release Micromatrices, Journal of Controlled Release, 5:271-283 (1988).

(Continued)

*Primary Examiner* — Michael M Bernshteyn
(74) *Attorney, Agent, or Firm* — Dardi & Herbert, PLLC; Curtis B. Herbert

(57) ABSTRACT

Certain embodiments of the invention include forming a material in situ by introducing into a space within a patient a water soluble polymer precursor of at least about 10,000 molecular weight solubilized in a flowable aqueous solution. Functional groups on the polymer precursor undergo covalent bonding in situ to form a solid and nonbiodegradable material having a swellability less than about 20% v/v and a Young's modulus of at least about 100 kPa within about 30 seconds to about 30 minutes of initiating a chemical reaction of the functional groups to form the solid material.

13 Claims, 5 Drawing Sheets

U.S. PATENT DOCUMENTS

| | | | |
|---|---|---|---|
| 6,299,597 B1 | 10/2001 | Buscemi et al. |
| 6,312,462 B1 | 11/2001 | McDermott et al. |
| 6,312,463 B1 | 11/2001 | Rourke et al. |
| 6,312,725 B1 | 11/2001 | Wallace et al. |
| 6,331,184 B1 | 12/2001 | Abrams |
| 6,334,869 B1 | 1/2002 | Leonhardt et al. |
| 6,371,975 B2 | 4/2002 | Cruise et al. |
| 6,379,373 B1 | 4/2002 | Sawhney et al. |
| 6,388,047 B1 | 5/2002 | Won et al. |
| 6,409,757 B1 | 6/2002 | Trout, III et al. |
| 6,458,889 B1 | 10/2002 | Trollsas et al. |
| 6,463,317 B1 | 10/2002 | Kucharczyk et al. |
| 6,495,127 B1 | 12/2002 | Wallace et al. |
| 6,506,204 B2 | 1/2003 | Mazzocchi |
| 6,514,534 B1 | 2/2003 | Sawhney |
| 6,517,824 B1 | 2/2003 | Kohn et al. |
| 6,534,591 B2 | 3/2003 | Rhee et al. |
| 6,544,276 B1 | 4/2003 | Azizi |
| 6,566,406 B1 | 5/2003 | Pathak et al. |
| 6,592,614 B2 | 7/2003 | Lenker et al. |
| 6,605,294 B2 | 8/2003 | Sawhney |
| 6,610,033 B1 | 8/2003 | Melanson et al. |
| 6,613,037 B2 | 9/2003 | Khosravi et al. |
| 6,632,457 B1 | 10/2003 | Sawhney |
| 6,639,014 B2 | 10/2003 | Pathak et al. |
| 6,656,214 B1 | 12/2003 | Fogarty et al. |
| 6,663,607 B2 | 12/2003 | Slaikeu et al. |
| 6,663,667 B2 | 12/2003 | Dehdashtian et al. |
| 6,673,093 B1 | 1/2004 | Sawhney |
| 6,703,047 B2 | 3/2004 | Sawhney et al. |
| 6,709,668 B2 | 3/2004 | Won et al. |
| 6,710,126 B1 | 3/2004 | Hirt et al. |
| 6,730,119 B1 | 5/2004 | Smalling |
| 6,818,018 B1 | 11/2004 | Sawhney |
| 6,827,735 B2 | 12/2004 | Greenberg |
| 6,843,803 B2 | 1/2005 | Ryan et al. |
| 6,887,974 B2 | 5/2005 | Pathak |
| 6,916,857 B2 | 7/2005 | Won et al. |
| 6,918,926 B2 | 7/2005 | Letort |
| 6,923,986 B2 | 8/2005 | Pathak et al. |
| 6,960,227 B2 | 11/2005 | Jones et al. |
| 6,962,979 B1 | 11/2005 | Rhee |
| 7,332,566 B2 | 2/2008 | Pathak et al. |
| 2002/0026217 A1 | 2/2002 | Baker et al. |
| 2002/0045848 A1 | 4/2002 | Jaafar et al. |
| 2002/0052643 A1 | 5/2002 | Wholey et al. |
| 2003/0012734 A1* | 1/2003 | Pathak et al. ............ 424/9.6 |
| 2003/0014075 A1 | 1/2003 | Rosenbluth et al. |
| 2003/0036745 A1 | 2/2003 | Khosravi et al. |
| 2003/0051735 A1 | 3/2003 | Pavcnik et al. |
| 2003/0130725 A1 | 7/2003 | DePalma et al. |
| 2003/0135269 A1 | 7/2003 | Swanstrom |
| 2003/0204242 A1 | 10/2003 | Zarins et al. |
| 2003/0204249 A1 | 10/2003 | Letort |
| 2003/0216802 A1 | 11/2003 | Chobotov et al. |
| 2004/0016997 A1 | 1/2004 | Ushio |
| 2004/0044358 A1 | 3/2004 | Khosravi et al. |
| 2004/0082989 A1 | 4/2004 | Cook et al. |
| 2004/0098096 A1 | 5/2004 | Eton |
| 2004/0131582 A1 | 7/2004 | Grinstaff et al. |
| 2004/0204755 A1 | 10/2004 | Robin |
| 2005/0004660 A1 | 1/2005 | Rosenbluth et al. |
| 2005/0028484 A1 | 2/2005 | Littlewood |
| 2005/0065592 A1 | 3/2005 | Holzer |
| 2005/0169882 A1 | 8/2005 | Lowe et al. |
| 2005/0271727 A1 | 12/2005 | Yao |
| 2006/0025853 A1 | 2/2006 | Evans et al. |
| 2006/0258698 A1 | 11/2006 | Mudumba et al. |
| 2008/0033471 A1 | 2/2008 | Paz et al. |

FOREIGN PATENT DOCUMENTS

| | | |
|---|---|---|
| EP | 1 704 878 A1 | 9/2006 |
| EP | 1 967 220 A2 | 9/2008 |
| WO | 98/12274 A1 | 3/1998 |
| WO | 98/35631 A1 | 8/1998 |
| WO | 99/03454 A1 | 1/1999 |
| WO | 99/08718 A3 | 2/1999 |
| WO | 99/22770 A1 | 5/1999 |
| WO | 99/34833 A1 | 7/1999 |
| WO | 99/59501 A1 | 11/1999 |
| WO | 00/09199 A1 | 2/2000 |
| WO | 00/12018 A1 | 3/2000 |
| WO | 00/51522 A1 | 9/2000 |
| WO | 01/21108 A1 | 3/2001 |
| WO | 01/66038 A2 | 9/2001 |
| WO | 02/102282 A1 | 12/2002 |
| WO | 2006/078770 A2 | 7/2006 |

OTHER PUBLICATIONS

Gayet et al., "High water content BSA-PEG hydrogel for controlled release device: Evaluation of the drug release properties", Journal of Controlled Release, 38:177-184 (1996).

Kissel et al., "ABA-triblock copolymers from biodegradable polyster A-blocks and hydrophilic poly(ethyleen oxide) B-blocks as a candidate for in situ forming hydrogel delivery systems for proteins", Advanced Drug Delivery Reviews, 54:99-134 (2002).

Sanabria-Delong et al., "Photo-Cross-Linked PLA-PEO-OLA Hydrogels from Self-Assembled Physical Networks: Mechanical Properties and Influence of Assumed Constitutive Relationships", Biomacromolecules, 9:2784-2791 (2008).

* cited by examiner

MATERIALS FORMABLE IN SITU WITHIN A MEDICAL DEVICE

CROSS REFERENCE TO RELATED APPLICATIONS

This application is a continuation of application Ser. No. 11/443,504, filed May 30, 2006, now U.S. Pat. No. 7,872,068, issued Jan. 18, 2011, which is hereby incorporated by reference herein.

FIELD OF THE INVENTION

The field of the invention relates to flowable precursors that form solid materials within an implanted medical device, for example an arterial prosthesis placed inside a natural blood vessel to treat an aneurysm.

BACKGROUND

Abdominal Aortic Aneurysms (AAA) are weakened areas in the aorta that form balloon-like bulges, or sacs, in approximately the abdominal area. As blood flows through the aorta, the pressure of the blood pushes against the weakened wall, causing it to enlarge. Blood pools in the enlarged area, usually without forming a firm clot. AAA is usually the result of degeneration in the media of the arterial wall, resulting in a slow and continuous dilatation of the lumen of the vessel. Ruptured AAA is about the 13th-leading cause of death in the United States, causing an estimated 15,000 deaths per year. While more than 500,000 Americans have been diagnosed with aortic aneurysms, less than 100,000 are treated due to shortcomings of current devices and the risk of open surgical procedures.

Clips and open surgery have been the traditional interventional treatments for AAA. More recently, less invasive techniques have been attempted, such as introducing a coil into the aneurysm that triggers blood clotting. Of those AAA's that are repaired, only about 30,000 procedures are minimally invasive. Other approaches have involved placing endografts across the aneurysm, so that blood can flow through the lumen of the graft and reduce the pressure on the aneurysm wall to prevent its enlargement and rupture. Stents have been used with the endografts to facilitate their placement and stabilize them in the patient. Conventional endograft devices, however, can be a poor fit for aneurysms, which can have complex three-dimensional geometries. Further, aneurysms can change shape over time leading to failure of an implanted graft and/or stent.

SUMMARY

What is needed is a technique for stabilizing AAA-treating devices. These techniques are described herein, including materials and methods of stabilizing implanted medical devices by introducing flowable precursor materials that expand an expandable member of the device to set the device in place, with the precursors then hardening to keep the device in place. A flowable filler creates the opportunity to expand an expandable member with adequate pressure to force the member against the surrounding tissue to conform to the shape of the tissue to create a good fit in a patient. Subsequent hardening of the filler locks the device in place. In the case of an AAA, an endograft equipped with suitable expandable members may be securely positioned with a lumen or lumens that allow blood to flow through the aorta and isolation of the aneurismal sac. The aneurismal sac, without blood flowing into it, is less likely to rupture and may remodel to a less dangerous condition, e.g., by collapsing around the endograft that bridges the sac. Other expandable and fillable devices for treating an AAA are described, for instance, in U.S. Pat. No. 6,312,462, in U.S. Pat. Pub. No. 2004/0204755 published Oct. 14 2004, and in U.S. application Ser. No. US2006/0025853A1 filed on Jul. 22, 2005 which are hereby incorporated herein by reference to the extent that they do not contradict explicit disclosure of this specification. As explained below, a filler for an expandable member should have certain characteristics.

Accordingly, certain embodiments of the technique are directed to a method of forming a material in situ in a biocompatible expandable member comprising, for instance, increasing a volume of an expandable member of a medical device within a patient by delivering a water soluble polymer precursor in a flowable aqueous solution into the expandable member. Functional groups on the polymer precursor undergo a single or combined mechanisms, such as covalent bonding, ionic complex, thermal transition, to form a solid and nonbiodegradable material having a swellability of less than about, e.g., 20% v/v and having a Young's modulus of at least about 1 kPa or at least about 10 kPa or at least about 100 kPa or at least about 1 MPa or at least about 10 MPa within about 30 seconds to about 30 minutes of initiating a chemical reaction of the functional groups to form the solid material, e.g., by free radical initiation or mixing another precursor having reactive functional groups with the first precursor. In some embodiments, the polymeric precursor comprises at least 100 MW or at least 4,000 MW of polyethylene oxide and acrylate functional groups. One variation includes using two precursors with molecular weights that are different by a factor of about 10, with the smaller precursor optionally having a molecular weight of less than about 2000 or less than about 1000. Materials formed by these techniques may have aqueous solvent intermixed therein, and may include intermixed buffering agents. Another variation includes changing the concentration of reactant solutions to obtain the hardened material.

Some embodiments of the invention relate to a medical device comprising an expandable member that comprises an aqueous buffered solution and a solid and nonbiodegradable polymeric material having a Young's modulus of at least about 10 kPa or at least about 100 kPa or at least about 1 MPa or at least about 10 MPa and a swellability of less than about, e.g., 20% v/v. An aqueous buffered solution or components of such a solution may be dispersed through the material or partially partitioned from the material.

DETAILED DESCRIPTION OF PREFERRED EMBODIMENTS OF THE INVENTION

Figure 1A:
FIG. 1A depicts a polymer precursor with two functional groups.

One embodiment of the invention is a system for forming polymeric materials in situ within an implantable medical device. As explained above, some implants can be stabilized in the body by introducing an implant with an expandable member that can be inflated with polymer precursors that form a solid material. The polymer precursors and resultant solid material may be chosen in light of a variety of considerations, including solubility in aqueous solution, viscosity, reaction time, heat of polymerization, shelf life, pot life, bonding to the medical device, and mechanical properties after polymerization such as tensile strength, low-swellability, compressive strength, stiffness, elasticity, brittleness, stability, and durability. Functional groups on the precursors may be chosen to address these and other design considerations. Other components of the system may be chosen to adjust these characteristics or to provide additional control over other pertinent factors, e.g., pH, durability, radiopacity, bonding to plastic, bonding to metal, and biocompatibility.

For treatment of AAA, an endograft comprising a thin, double-walled balloon can be placed across the AAA with an inner lumen of the endograft providing for blood flow through the endograft. The balloon is filled in-situ with flowable polymeric precursors that polymerize and harden into a solid material. The hardened material is conformed to the specific shape of the patient's aneurysm and provides stability, a leak-proof seal, and prevents migration of the endograft.

The polymer precursor is a polymer that has reactive functional groups that form covalent bonds with particular functional groups on other polymer precursors to thereby form a polymeric material. The polymer precursor may be any polymer or a synthetic polymer. Synthetic is a term that refers to molecules not naturally produced by a human cell and excludes, for example, collagen regardless of how it is made or how it is chemically modified. Some polymer precursors may be essentially synthetic meaning that they are at least about 90% by molecular weight synthetic with the balance of the precursor being chemical groups with a biological motif, e.g., a sequence of amino acids degradable by particular enzymes. Polymer precursors may be selected to be free of amino acids, or peptide bonds, or saccharide units, or polysaccharides.

Polymer precursors may comprise a variety of polymeric groups. Some precursors are water soluble, meaning that the precursors are soluble in aqueous solution at a concentration of at least about 1 gram per liter. Some precursors comprise polyethylene oxide (PEO, —$(CH_2CH_2O)_n$—), which is useful to impart water solubility and desirable viscosity in solution and mechanical properties when formed into a polymeric material. Some polymer precursors comprise, e.g., about 100 to about 500,000 MW of PEO; the ordinary artisan will understand that all values and subranges within these explicitly articulated values are included, e.g., about 600 Daltons, about 15,000 Daltons, about 500 to about 100,000 Daltons, about 5,000 to about 50,000 Daltons. Some precursors include comparable amounts of polymers related to PEO, e.g., polypropylene oxide (PPO, —$CH_2(CH_2)_2O)_n$—), other polyalkylene oxide, or a copolymer of PEO-PPO, e.g., about 100 to about 250,000 Daltons. Water-soluble precursors may also be formed directly from, or after derivitization of, other polymers, e.g., poly(acrylic acid), polyvinyl alcohol), polyvinyl chloride, polyacrlonitrile, polyallyamine, polyacrylates, polyurethanes, polycarbomethylsilane, polydimethylsiloxane, polyvinylcaprolactam, polyvinylpyrrolidone, or a combination of these. For example, a nonwater soluble polymer may be decorated with water soluble groups to enhance its water solubility to make a water soluble polymer precursor, e.g., by adding carboxyls, hydroxyls, or polyethylene glycols. Examples of water soluble monomers that may be used to are 2(2-ethoxyethoxy) ethyl acrylate, ethoxylated (15) trimethylolpropane triacrylate, ethoxylated (30) bisphenol a diacrylate, ethoxylated (30) bisphenol a dimethacrylate, ethoxylated (20) trimethylolpropane triacrylate, metallic diacrylate, methoxy polyethylene glycol (350) monoacrylate, methoxy polyethylene glycol (350) monomethacrylate, methoxy polyethylene glycol (550) monoacrylate, methoxy polyethylene glycol (550) monomethacrylate, polyethylene glycol (200) diacrylate, polyethylene glycol (400) diacrylate, polyethylene glycol (400) dimethacrylate, polyethylene glycol (600) diacrylate, polyethylene glycol (600) dimethacrylate, and polypropylene glycol monomethacrylate.

Polymer precursors may be linear or be branched. For example, the precursor may have 3 or more termini, e.g., at least 3, or about 3 to about 12, artisans will immediately appreciate that all ranges and values within the explicitly stated ranges are disclosed. A variety of techniques and sources for obtaining multi-armed precursors and attaching functional groups to them are known, e.g., as in the Aldrich catalog or Nektar or Shearwater Polymers or from Sartomer, Inc. catalogs, as well as in the literature for these arts.

Some embodiments include two or more precursors with distinct average molecular weights or two or more types of precursors. Different types of precursors have distinct chemical formulae. A single type of polymer may be incorporated into two polymeric precursors having two distinct average molecular weights. Molecular weight averages for a solution of precursors may be determined as is customary in these arts, e.g., by weight or number averaging. Accordingly, a molecular weight for a precursor represents an average molecular weight for a plurality of precursors.

A precursor's functional groups may be, for example, polymerizable or reactive by electrophile-nucleophile combination. The groups may be reactive with identical groups, e.g., as in free radical polymerization of acrylates, or with complementary groups, e.g., as in electrophilic-nucleophilic reactions. Polymerizable groups include, e.g., ethylenically unsaturated groups, groups polymerizable by free-radical chemistry, condensation chemistry, or addition chemistry. Examples of functional groups are: acrylates, methacrylates, butyl acrylate, methyl methacrylate; butyl methacrylate, hydroxyethyl methacrylate, polypropylene glycol diglycidal ether, polyethylene glycol diglycidyl ether, N-acryloxysuccinimide, glycidyl methacrylate, and hexamethylene diisocyanate. Examples of electrophilic or nucleophilic functional groups include succinimide esters, maleic acids, isocyanates, maleic acids, carbodiimides, aldehydes, azos, diazos, thiocyanates, carboxyls, amines, thiols, and hydroxyls. The functional groups on a precursor may be the same or of different types, with each type of functional group being a chemically distinct group. Different types of precursors may have the same or different types of functional groups, provided that the precursors react to form a polymeric material.

In some embodiments, acrylates may advantageously be used because acrylates are generally water soluble but do not react with water. In contrast, for example, a polyurethane precursor will react with water. Also, acrylamide monomers are generally toxic, while water soluble acrylates have a low toxicity and are more acceptable for biomedical applications involving implantation.

Figure 1B:
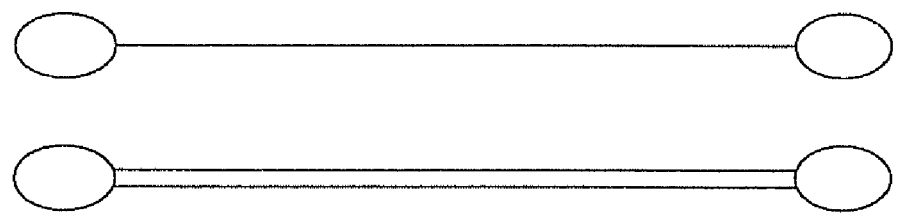
FIG. 1B depicts two types of polymer precursors with chemically distinct backbones and similar functional groups.
Figure 1C:
FIG. 1C depicts a polymer precursor with two types of functional groups.
Figure 1D:
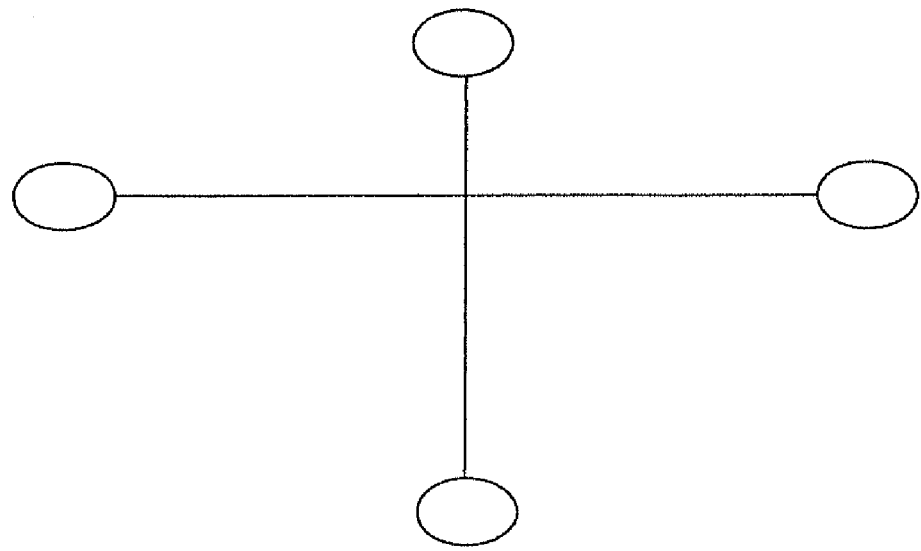
FIG. 1D depicts a multi-armed polymer precursor with four functional groups.
Figure 1E:
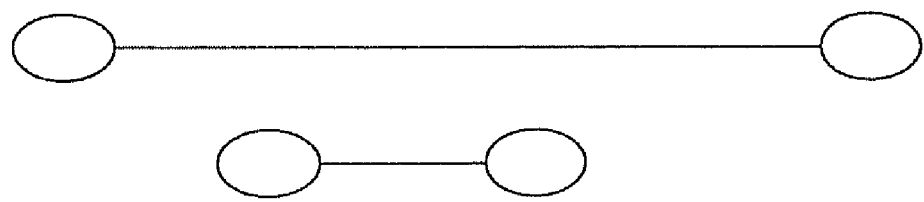
FIG. 1E depicts two polymer precursors of different molecular weights.
Figure 1F:
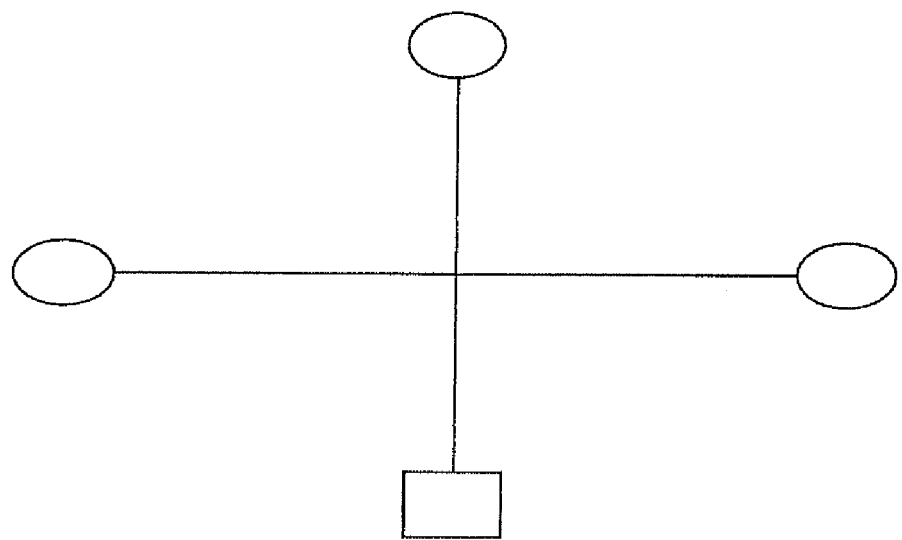
FIG. 1F depicts a multi-armed polymer precursor with two types of functional groups.
Figure 1G:
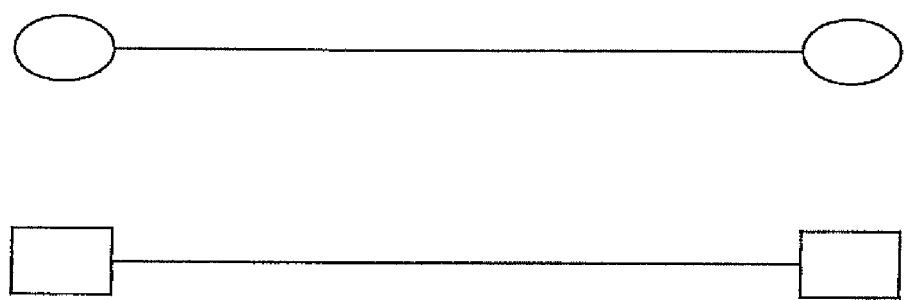
FIG. 1G depicts two polymer precursors with two types of functional groups.
Figure 2:
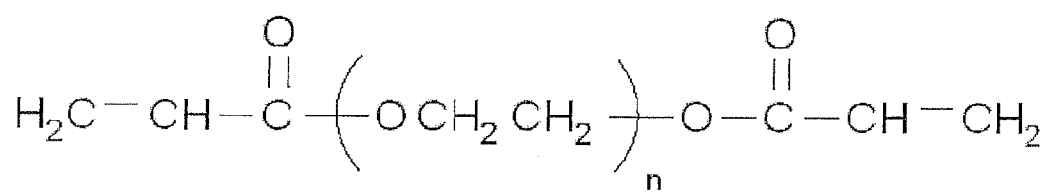
FIG. 2 depicts a polymer precursor with a polyethylene glycol backbone and acrylate functional groups.
Figure 3:
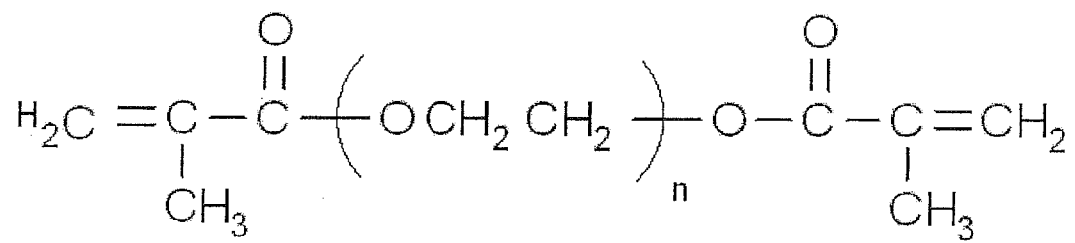
FIG. 3 depicts a polymer precursor with a polyethylene glycol backbone and methacrylate functional groups.
Figure 4:
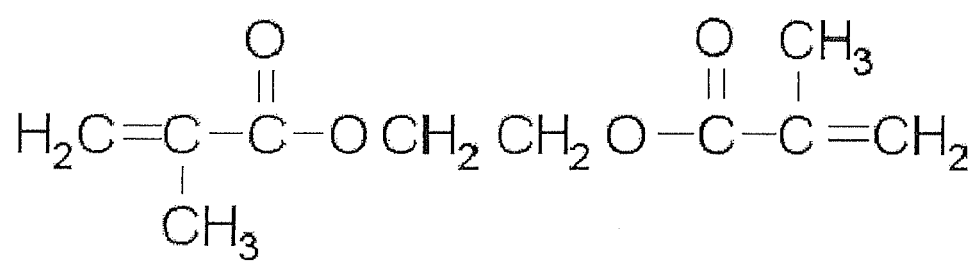
FIG. 4 depicts a polymer precursor with methacrylate functional groups.
Figure 5:
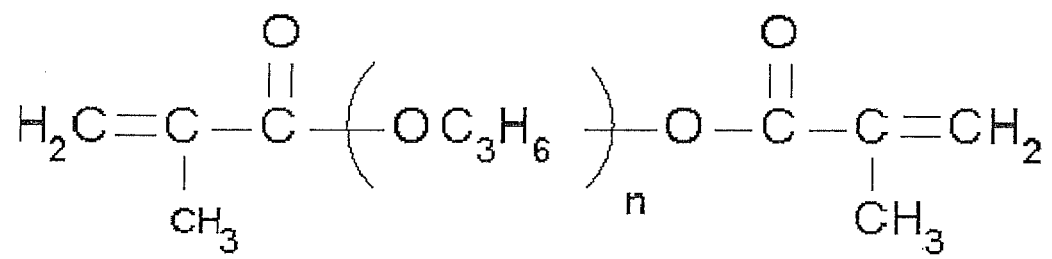
FIG. 5 depicts a polymer precursor with a polypropylene backbone and methacrylate functional groups.

For example, FIG. 1A depicts a polymer precursor with two functional groups that have the same chemical formula, with the functional groups being reactable to form a solid material, e.g., by free radical polymerization. And FIG. 1B shows two types of polymer precursors with chemically distinct backbones that both have the same type of functional group, with the two precursors being reactable with each other to form a solid material. FIG. 1C depicts a set of polymer precursors with different functional groups that can react to form a solid material, e.g., by free radial polymerization or electrophilic-nucleophilic reaction. Other variations include, for example, a multi-armed precursor terminated with the same type of functional group (FIG. 1D), a set of precursors with similar backbones of different molecular weight and having the same functional groups (FIG. 1E), a multi-armed precursor with different types of functional groups, e.g., for free radical polymerization or electrophilic-nucleophilic reaction (FIG. 1F), or a set of precursors with distinct functional groups (FIG. 1G). FIG. 2 depicts an exemplary polymer precursor having a PEG backbone and acrylate functional groups. FIG. 3 depicts an exemplary polymer precursor having a PEG backbone and methacrylate functional groups. FIG. 4 depicts an exemplary polymer precursor having methacrylate functional groups reacted with a diglycol. FIG. 5 depicts an exemplary polymer precursor having a polypropylene backbone and methacrylate functional groups Some embodiments employ combinations of polymer precursors with large variations in molecular weight. A small precursor can be relatively more mobile than an end of a larger precursor so that fewer living chains are terminated without reaction. Further, a small precursor can be used to control physical properties of a material generated from the larger precursor, e.g., to adjust stiffness or other properties controlled by the number and distance between chain crosslinks. For instance, a lower molecular weight precursor can enhance the stiffness of a polymeric material by providing shorter distances between crosslinks. Thus some embodiments include a first precursor with a molecular weight of about 30,000 to about 300,000 and a second precursor with a molecular weight between about 100 and about 3,000. Other embodiments use a precursor with a molecular weight that is about 10 to about 100 times less than the molecular weight of a second precursor or, alternatively, less than the molecular weight of all the other precursors in the system. For instance, a first precursor having free radical polymerizable functional groups can be mixed with a relatively lower molecular weight precursor having free radical polymerizable functional groups. When polymeric precursors are reacted, they form polymer segments in the polymeric material. Thus a 30,000 MW bifunctional polymer precursor can form a polymer segment of 30,000 MW in the material.

The time required for polymer precursors to react may be controlled by the choice of functional groups, precursor size, pH, initiator, catalyst, or accelerants. In general, a time of between about 30 seconds to about 30 minutes for polymerization is desired so that the precursor solution or solutions may be introduced into the medical device without undue increases in viscosity and without unduly extending the procedure time required for the precursors to form a firm material that permits users to close the patient. The time to polymerization may be measured outside a patient by observing the time from activation of precursors in a solution or suspension until the solution or suspension is no longer flowable. Activation of the precursors refers to the event that triggers their reaction with each other, e.g., initiating a free radical polymerization or mixing electrophilic and nucleophilic groups at a reactive pH.

Bonding of the polymeric material to the device may be controlled by selecting precursor functional groups and/or precursors to bond the expandable member, or members that receive the precursors or mixed precursors. Bonding to plastic and metal may be enhanced by using suitable functional groups, e.g., sodium acrylates or other metallic acrylates.

The material formed upon reaction of polymer precursors should have adequate mechanical properties to keep the device stable within the patient. Thus materials that are stiff enough to resist deformation caused by forces applied to the device after implantation are advantageous. Embodiments include materials with a Young's modulus of at least about 500 kPa, or 1000 kPa, or in a range of about 500 kPa to about 50,000 kPa; artisans will immediately appreciate that other values may be suitable and that all values and ranges within the explicitly articulated ranges are disclosed. Modulus is measured as follows: Cylindrical shaped samples of the crosslinked polymer are created by injecting the polymeric mixture into a silicone tubing of a known inner diameter. After time required to substantially complete crosslinking has elapsed, 1 cm high cylindrical "discs" are cut from the tubing using a sharp razor blade; alternatively, tubing of 1-cm in length is used so that no cutting is necessary. The discs are carefully removed, avoiding cracking the samples and ensuring they are free of bubbles and edge defects. The discs are then subjected to a crush test in an Instron universal materials testing machine using a flat compression plate and using a 500N load cell. The modulus can be calculated using the extension and load data obtained during the preloading step where the stress strain curve is linear. The Load (N) divided by the plug cross sectional area (in meters square) gives the stress (Pa), while the amount of preload compression (Extension, mm) divided by the plug length (mm) gives the strain (no units). Modulus can then be calculated by dividing Stress with Strain. The ultimate strain can be computed as follows:

Ultimate percent strain is then total plug compression divided by plug length, times 100.

Total plug compression (mm)=Extension (mm)+displacement (mm)

Percent strain=[Total plug compression (mm)/plug length (mm)]*100

The maximum stress attained is the ultimate stress.

Certain embodiments are non-hydrogels. Certain embodiments are polymers formed from the precursors and functional groups set forth herein, as well as combinations thereof, e.g., polyacrylates, polymethacrylates, and polymethylmethacrylates. Materials that have a high ultimate stress and strain and which still have a modulus above about 100 kPa) are preferred. Materials that do not show substantial hydration upon being placed in an aqueous environment and also do not exhibit substantial degradation in physical properties over time are preferred.

The material formed upon reaction of polymer precursors should have adequate durability to keep the device stable within the patient over time. Some embodiments of the material effectively maintain their mechanical properties over a period of at least 5, 10, 15, 20, or 30 years. Some embodiments of the polymeric material are essentially not biodegradable in an animal body, i.e. are not subject to effective hydrolytic and/or enzymatic degradation that leads to a loss of mechanical strength in an animal body in a typical tissue, i.e., as measurable by implantation subcutaneously, intramuscularly, or intravascularly in an animal model such as a rat or a rabbit. Examples of nonbiodedgrabale polymeric materials are polyacrylates, polymethacrylates, and polymethylmethacrylates. Examples of biodegradable materials are fibrin glue, hyaluronic acid, collagen, polylactic acid, and many polyesters.

The polymeric material may be designed to have limited swellability in aqueous solution. A limited degree of swelling advantageously prevents the polymeric material from applying pressure to its surroundings after formation, even if water is present. And limited intake of water through swelling can help to keep the material immobile in the patient. Certain embodiments of the polymeric materials have a swelling in aqueous solution of less than 20% v/v, 10% v/v, 5% v/v, or 1% v/v, as measured by exposing the polymeric material to a 300-330 milliOsmolar, pH 7.4 buffered water solution after the polymeric material essentially reaches its full compressive strength and observing its change in weight after it has been allowed to swell in an unconstrained state for 24 hours, with the volume swelling being calculated from the change in weight.

Viscosity of solutions of the polymer precursors can be controlled by adjusting factors such as the type of polymer, the polymer concentration, solubility of the polymer, and the polymer's molecular weight. In general, the viscosity of a precursor solution should be low enough to allow the solution to be forced down a tube, e.g., a hollow tube guidewire, that allows inflation of an endograft using medically safe pressures. Some medical devices use such tubes to inflate balloons on endoscopic devices, e.g., for angioplasty or temporary occlusion of a blood vessel. In general, viscosities of less than about 500 centipoise, less than about 100 centipoise, or less than about 10 centipoise, are preferable. The viscosity may be adjusted for use in conventionally-sized tubes, with conventional operating pressures of less than about 25 atmospheres.

Some embodiments of the precursors are chosen with functional groups that are reactable at an approximately physiological pH and/or osmolarity. These characteristics are useful, for instance, for employing physiological buffers to solubilize the precursors, push the precursors into place, or to flush a portion of the device with precursors or polymeric material in place. When two or more solutions of precursors are mixed, buffers for one or more of the solutions may be chosen to have a first pH before mixing and a second pH after mixing. For example, a first precursor solution may have a low pH in a low buffering strength buffer to minimize reaction of the precursors and a second solution with a relatively higher buffering strength may be mixed with the first solution to achieve a second pH that is favorable for reaction of the precursors. Additionally, the ester linkages are observed to be more stable at somewhat acidic pH (e.g., about pH 4) and so a particular pH may be selected for certain components for reasons of stability. Upon implantation, a physiological pH of (e.g., about 7 to about 8) may be chosen for biocompatibility reasons. Alternatively a different pH may be chosen, e.g., from about 4 to about 9.

Radio-opaque components may be introduced with polymeric precursors to allow visualization of the polymeric material after it is formed. Examples of radio-opaque materials are PANTOPAQUE, barium sulfate, tantalum powder, (all water insoluble), ISOVUE, OXILAN, iodapamide, omnipaque, metrizamide, iopentol, iohexol, iophenoxic acid, ioversol, gadodiamide, and sodium tyropanoate. Components may be introduced to enhance imaging, for example, according to X-ray, magnetic resonance imaging, and tomography, e.g., spiral computer tomography techniques.

Some embodiments of the functional groups are free radical polymerizable groups that may advantageously be exposed to initiators and/or catalysts to, for example, enhance reaction kinetics or mechanical properties of the polymeric material.

Initiators are required to start polymerization in many systems, and include, for example, thermal, chemical, and light-activated initiators. Initiators may be used to activate the polymer precursors to polymerize and form the polymeric material. Initiator concentration can affect variables such as polymerization time, temperature, and mechanical properties of the polymeric material.

In reduction-oxidation chemical initiating systems, for example, metal ions may be used either as an oxidizer or a reducer. For example, certain metal ions may be used in combination with a peroxide or hydroperoxide to initiate polymerization. Some suitable metal ions have at least two states separated by only one difference in charge, e.g., ferric/ferrous; cupric/cuprous; ceric/cerous; cobaltic/cobaltous; vanadate V vs. IV; permanganate; and manganic/manganous. Peroxygen containing compounds, such as peroxides and hydroperoxides, including hydrogen peroxide, t-butyl hydroperoxide, t-butyl peroxide, benzoyl peroxide, cumyl peroxide, may also be used.

Thermal initiating systems may also be used, for example, commercially available low temperature free radical initiators that initiate free radical crosslinking reactions at or near physiological body temperatures. Some examples are sodium persulfate (50° C.), ammonium persulfate (50° C.), glucose oxidase-glucose-ferrous sulfate (initiated around 37° C. in presence of dissolved oxygen).

Photoinitiators are also known for initiation of polymerization, e.g., DAROCUR 2959 (initiated around 360 nm), IRGACURE 651 (initiated around 360 nm), eosin-triethanol amine (initiated around 510 nm), methylene blue-triethanol amine (initiated around 632 nm), and the like.

Catalysts, co-catalysts, and chain extenders may be used to further control reaction of the polymer precursors or to extend shelf life. For example, small amounts of vinyl pyrrolidinone (e.g., around 1-10 µl per ml) can be added while using eosin-triethanol photoinitiating system. Inhibitors such as hydroquinone may be added to prevent premature polymerization of polymer precursors during storage. Tetramethylethylenediamine (TEMED) is a catalyst useful in many polymerizations, e.g., in an ammonium persulfate/TEMED or riboflavin/TEMED catalyzed reaction. Some initiators can be chosen that require little or no oxygen, e.g., riboflavin-based initiator systems. Systems that are not substantially inhibited by the presence of oxygen and that can enable the reaction to proceed at physiological temperature may be chosen.

Delivery of polymeric precursors in aqueous solution facilitates preparation of a solution with a controlled viscosity by including water. Further, an aqueous solution, as opposed to, e.g., an organic solvent, provides safety benefits in case some amount of the solution should be exposed to the patient or user. The presence of water also serves to reduce the mass of polymerizable precursors used, and thus improves the toxicological profile of the precursors, should they be accidentally discharged into the body. Further, an aqueous solvent for the precursors is avoids potential compatibility problems with materials used in the expandable device, such as degradation of the material or potentially unwanted changes to its mechanical properties, e.g., softening by partial salvation. In general, aqueous solutions do not solvate biomaterials used for an expandable member of a medical device. The aqueous solvent may be interspersed through the polymeric material, e.g., in pore spaces, or some portion of the solvent may be partitioned away from the material. The solvent may be buffered with a buffering agent or agents to control pH of the solution. The amount of aqueous solvent to mix with the other components of the system may be adjusted to achieve a desired viscosity in light of the properties of the hardened material. Some embodiments include between about 0.5 parts to about 10 parts by weight of polymeric precursor compared to the weight of the aqueous solvent; artisans in this field will immediately appreciate that all ranges and values within this range are disclosed.

The polymer precursors may be used to fill an expansion member of an implantable medical device. The medical device may be, for example, suited for minimally invasive surgery (MIS) techniques, e.g., guidable through vasculature of a human patient using a guidewire introduced into the patient for that purpose. Examples of MIS devices having an inflatable or expandable member or are provided in, for example, PCT Application Pub. No. WO 00/51522, U.S. Pat. Nos. 5,334,024, 5,330,528, 6,312,462, 6,964,667, 7,001,431, in U.S. Pat. Pub. No. 2004/0204755 published Oct. 14 2004, and U.S. Patent Ser. No. US2006/0025853A1 filed on Jul. 22, 2005, which are hereby incorporated by reference herein to the extent that they do not contradict what is explicitly disclosed herein.

An expandable member undergoes an increase in volume resulting from introduction of a flowable material into the member. An expandable member may be, for example, a balloon, a double-walled balloon, or an inflatable cuff. The expandable member may include either compliant materials, or non-compliant materials, or both. A non-compliant material generally resists deformation under physiological conditions, e.g., parylene, polytetrafluoroethylene, or polyethylene terephthalate. Examples of compliant materials are silicones, latexes, and elastic materials in general. A noncompliant material may be used in an expandable member by introducing the material in a shape that allows for subsequent expansion; for example, a noncompliant material be coiled or folded for delivery and expanded by uncoiling or unfolding, e.g., as a result of filling the member with a flowable precursor. A balloon used for placement of an implantable medical device may be a sealed, flexible, expandable member that is elastic. Balloons may take a wide variety of shapes, e.g., including spherical, ellipsoidal, tubular, cylindrical (filled between double walls with a lumen interior to the cylinder). Expandable members may include a combination of compliant materials and noncompliant materials, e.g., a noncompliant portion adjoined to a complaint portion.

In use, polymer precursors in a flowable form may be delivered to an expandable member wherein they are solidified into a polymeric material. The flowable precursors may be introduced into the expansion member to expand a flexible material to increase a volume of the member, which may be sealed after it is expanded. The material within the member is may be referred to as being within the patient even though the material does not directly contact a patient's tissue. Expansion of the member may force the member against a tissue of the patient to seat the device in the tissue. Hardening of the precursors into a solid material further secures the device. The precursor or precursors may be activated before, during, or after introduction into the expansion member. Activation beforehand may be accomplished by mixing a polymeric precursor with an activating agent that causes precursors to form covalent bonds, for example, as an initiator that initiates polymerization, a buffer that changes a pH of a precursor-and-initiator solution to activate the initiator, or external energy in the form of heat or light may be applied to activate a thermal or photoinitiator. And, for example, electrophilic-nucleophilic reactions may be activated by mixing a precursor with electrophilic functional groups with a precursor having nucleophilic functional groups, or by using a buffer to change the pH of a premixed combination of precursors with electrophilic and nucleophilic functional groups.

In some embodiments, two solutions are mixed with each other ex vivo and introduced using MIS techniques into an expandable member. The mixture is pumped through a filling tube into the expandable member until a desired pressure is achieved, and the tubes for filling the member are withdrawn, leaving the expandable member inflated with the mixture, which is sealed entirely within the member and hardens into a solid material, e.g., a polymeric material, with the time to polymerization being greater than the amount of time required to fill the member and withdraw the filling tube. An example of this method is combining a first container having a polymerizable first precursor with a solution having an initiator that initiates polymerization. As explained above, various types and sizes of precursors may be used in combination with various types of initiators. For instance, two solutions with different types and/or molecular weights of precursors may be used.

In other embodiments, two solutions are prepared that are separately introduced via separate filling tubes for combination within the patient, e.g., mixing for the first time in the expandable member or in a manifold disposed in the introductory device.

By way of example, a kit may be prepared with a first precursor container having about 10 grams of a 35,000 MW PEG polymeric precursor terminated with a diacrylate functional group at each of two ends. The first precursor container may contain a radio-opaque agent, e.g., about 10 grams sodium diatrizoate, and an initiator, e.g., about 1.8 grams of a persulfate. A first diluent container has about 230 ml of phosphate buffered solution at physiological pH (e.g., 7.4) and physiological osmolarity, or an osmolarity and buffering strength that achieves physiological pH and osmolarity after combination with other components. A second precursor container has about 150 ml of essentially pure 600 MW PEG polymeric precursor terminated with a diacrylate functional group at each of two ends, and further comprises 100 ml of phosphate buffered solution pH 4 and a catalyst, e.g., about 1.8 ml of TEMED. A user mixes the first diluent container with the first precursor container to form a first precursor solution that is mixed with the contents of the second precursor container and used to fill an expandable member. The precursors form a hard firm crosslinked material in approximately 2-3 minutes. The material is visible on x-ray fluoroscopy due to the sodium Diatrizoate. As described above, the system may be controlled to produce faster or shorter polymerization time, e.g., from about 30 seconds to about 30 minutes for either or both. For instance, about 1.2 g of persulfate and 1.2 ml of TEMED would provide approximately a 5-6 min polymerization time. Or about 0.6 g of persulfate and about 0.6 ml of TEMED in the same formulation would result in a polymerization time of about 20 minutes.

As already discussed, other variations include, for example, replacing PEG 600DA with ethoxylated trimethylolpropane triacrylate or ethoxylated pentaerythritol tetraacrylate, changing solids concentrations, use of alternative radiopacifiers, using other initiation systems (e.g., iron salts and hydrogen peroxide), or adding comonomers that promote adhesion to plastic.

Certain other embodiments involve using a filler material mixed with polymeric precursor(s) to form a polymeric material that includes a filler. A filler can be used to adjust the properties of the polymeric material, for example, the stiffness, mechanical strength, compressibility, or density. Examples of fillers include solid objects, e.g., beads, cylinders, microbeads, hollow materials, e.g., hollow microspheres, fibers, e.g., polylactic acid fibers, and meshes, e.g., nylon meshes. Such fillers may be mixed with one or both of the precursors before introduction into an implant, or the fillers may be admixed in situ. The precursor solutions may be used as a continuous suspending medium to hold the filler in place.

It is claimed:

1. A method of forming a material in situ comprising:
introducing into a space within a patient a water soluble polymer precursor having a molecular weight at least about 400 Daltons solubilized in a flowable aqueous solution, wherein functional groups on the polymer precursor undergo covalent bonding to form a solid and nonbiodegradable material having a swellability less than about 20% v/v and a Young's modulus of at least about 100 kiloPascals within about 30 seconds to about 30 minutes of initiating a chemical reaction of the functional groups to form the solid material.

2. The method of claim 1 wherein the polymeric precursor comprises of polyethylene oxide having a molecular weight at least 100 Daltons.

3. The method of claim 1 wherein the functional group comprises an acrylate.

4. The method of claim 1 wherein the viscosity of the flowable solution is less than about 100 cp.

5. The method of claim 1 wherein the functional groups are of a first type and further comprising a second type of functional groups on a second polymeric precursor that react to form covalent bonds with the first type of functional groups.

6. The method of claim 5 wherein the first polymeric precursor has a molecular weight of at least about 10,000 Daltons and the second polymeric precursor has a molecular weight of less than about 3000 Daltons.

7. The method of claim 1 wherein initiating the chemical reaction comprises mixing the polymeric precursor with a polymerization initiator.

8. The method of claim 1 wherein the solution further comprises a radio-opaque agent for imaging the material.

9. The method of claim 1 wherein the functional groups are electrophilic or nucleophilic.

10. The method of claim 1 wherein the functional groups are polymerizable by free radical polymerization.

11. The method of claim 1 wherein the material has a Young's modulus of at least 10 kPa within 30 seconds to 10 minutes of initiating the chemical reaction of the functional groups.

12. The method of claim 1 wherein the expandable member comprises a balloon or a cuff.

13. The method of claim 1 wherein the polymeric precursor is present at a range of between about 0.1 parts to about 10 parts by weight of polymeric precursor compared to the weight of the aqueous solvent in the solution.

* * * * *